United States Patent
Yokhin et al.

(10) Patent No.: US 7,600,916 B2
(45) Date of Patent: Oct. 13, 2009

(54) TARGET ALIGNMENT FOR X-RAY SCATTERING MEASUREMENTS

(75) Inventors: Boris Yokhin, Nazareth Illit (IL); Alexander Krokhmal, Haifa (IL); Asher Peled, Eyen Yehuda (IL); David Berman, Kiryat Tivon (IL)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 237 days.

(21) Appl. No.: 11/892,005

(22) Filed: Aug. 17, 2007

(65) Prior Publication Data

US 2007/0286344 A1    Dec. 13, 2007

Related U.S. Application Data

(63) Continuation-in-part of application No. 11/000,044, filed on Dec. 1, 2004, now Pat. No. 7,474,732.

(51) Int. Cl.
   *A61B 6/08* (2006.01)
   *G01N 23/201* (2006.01)
(52) U.S. Cl. .......................................... 378/205; 378/86
(58) Field of Classification Search ...................... 378/4, 378/7, 71, 74, 70, 86–90, 98.8, 206–207
   See application file for complete search history.

(56) References Cited

U.S. PATENT DOCUMENTS

| | | | |
|---|---|---|---|
| 4,725,963 A | 2/1988 | Taylor et al. | |
| 4,989,226 A | 1/1991 | Woodbury et al. | |
| 5,151,588 A | 9/1992 | Kiri et al. | |
| 5,574,284 A | 11/1996 | Farr | |
| 5,619,548 A | 4/1997 | Koppel | |
| 5,740,226 A | 4/1998 | Komiya et al. | |
| 5,949,847 A | 9/1999 | Terada et al. | |
| 5,963,329 A | 10/1999 | Conrad et al. | |
| 6,041,098 A | 3/2000 | Touryanski et al. | |
| 6,192,103 B1 | 2/2001 | Wormington et al. | |
| 6,226,347 B1 | 5/2001 | Golenhofen | |
| 6,226,349 B1 | 5/2001 | Schuster et al. | |
| 6,381,303 B1 | 4/2002 | Vu et al. | |
| 6,389,102 B2 | 5/2002 | Mazor et al. | |
| 6,453,006 B1 | 9/2002 | Koppel et al. | |

(Continued)

FOREIGN PATENT DOCUMENTS

JP    9-308339    12/1997

(Continued)

OTHER PUBLICATIONS

Wiener et al., "Characterization of Titanium Nitride Layers by Grazing-Emission X-Ray Fluorescence Spectrometry", in Applied Surface Science 125 (1998), p. 129-136.

(Continued)

*Primary Examiner*—Irakli Kiknadze
(74) *Attorney, Agent, or Firm*—Smith, Gambrell & Russell, LLP (57) ABSTRACT

A method for X-ray analysis of a sample includes directing a beam of X-rays to impinge on a structure in the sample such that the X-rays are scattered from the structure in a pattern of stripes, and receiving the scattered X-rays using an array of detectors. A relative alignment between the sample and the array is adjusted so that the stripes are parallel to the detectors.

20 Claims, 4 Drawing Sheets

U.S. PATENT DOCUMENTS

| | | | |
|---|---|---|---|
| 6,507,634 | B1 | 1/2003 | Koppel et al. |
| 6,512,814 | B2 | 1/2003 | Yokhin et al. |
| 6,556,652 | B1 | 4/2003 | Mazor et al. |
| 6,639,968 | B2 | 10/2003 | Yokhin et al. |
| 6,643,354 | B2 | 11/2003 | Koppel et al. |
| 6,680,996 | B2 | 1/2004 | Yokhin et al. |
| 6,711,232 | B1 | 3/2004 | Janik |
| 6,744,950 | B2 | 6/2004 | Aleksoff |
| 6,750,952 | B2 | 6/2004 | Grodnensky et al. |
| 6,771,735 | B2 | 8/2004 | Janik et al. |
| 6,895,075 | B2 | 5/2005 | Yohkhin et al. |
| 7,110,491 | B2 | 9/2006 | Mazor et al. |
| 2001/0028699 | A1 | 10/2001 | Iwasaki |
| 2001/0043668 | A1 | 11/2001 | Hayashi et al. |
| 2002/0080922 | A1* | 6/2002 | Kwasnick et al. .......... 378/205 |
| 2002/0097837 | A1 | 7/2002 | Fanton et al. |
| 2002/0110218 | A1 | 8/2002 | Koppel et al. |
| 2003/0157559 | A1 | 8/2003 | Omote et al. |
| 2004/0052330 | A1 | 3/2004 | Koppel et al. |
| 2004/0156474 | A1 | 8/2004 | Yokhin et al. |
| 2004/0218717 | A1 | 11/2004 | Koppel et al. |
| 2006/0115046 | A1 | 6/2006 | Berman et al. |

OTHER PUBLICATIONS

Hayashi et al., "Refracted X-Rays Propagating Near the Surface under Grazing Incidence Condition", Spectrochimica Acta, Part B 54, 1999, pp. 227-230.

Series 5000 Model XTF5011 X-Ray Tube Information, Oxford Instruments Inc., Scotts Valley, GA, U.S.A., Jun. 1998.

Monolithic Polycapillary Lens Information, X-Ray Optical Systems, Inc., Albany, NY, U.S.A., Dec. 29, 1998. (web site: www.xos.com).

S. Di Fonzo et al., "Non-Destructive Determination of Local Strain with 100-Nanometre Spatial Resolution", Nature, vol. 403, Feb. 10, 2000. (web site: www.nature.com).

Hugues Guerault, "Specular reflectivity and off-specular scattering", Tools for roughness investigation, Dec. 2000.

Jones, et al., "Small angle x-ray scattering for sub-100 nm pattern characterization", Applied Physics Letters 83:19 (2003), pp. 4059-4061.

Hu et al., "Small angle x-ray scattering metrology for sidewall angle and cross section of nanometer scale line gratings", Journal of Applied Physics 96:4 (2004), pp. 1983-1987.

Kojima, et al., "Structural characterization of thin films by x-ray reflectivity", Rigaku Journal 16:2 (1999), pp. 31-41.

Stommer, "X-ray scattering from silicon surfaces", in Semiconductor International (May 1, 1998).

Yoneda, "Anomalous surface reflection of X Rays", Physical Review 131, pp. 2010-2013, 1963.

Stommer, et al., "Characterization of semiconductor materials by X-ray scattering", Electrochemical Society Proceedings vol. 99-16, pp. 117-133, 1999.

Bowen, et al., "X-Ray metrology by diffraction and reflectivity", Characterization and Metrology for ULSI Technology, 2000 International Conference (American Institute of Physics, 2001). pp. 570-579.

Ulyanekov, "Introduction to high resolution X-Ray diffraction", Workshop on X-ray characterization of thin layers (Uckley, May 21-23, 2003).

Ito, "X-ray Scattering Method for Determining Pore-Size Distribution in Low-k Thin Films", Presented at the International Sematech Ultra-Low-k Workshop (San Francisco, CA, Jun. 6-7, 2002).

Naudon, et al., "New apparatus for grazing X-ray reflectometry in the angle-resoived dispresive mode", J. Appl. Cryst. 1989, vol. 22, pp. 460-464.

N. Wu, et al, "Substepping and its Application to HST Imaging", Jul. 28, 2003.

Wormington, Characterization of Pore Size Distribution in Low k Dielectrics Using X-ray Reflectivity, presented at the Sematech Gate Stack Engineering Workshop (Austin, Texas, May 2, 2002).

J. Spear, "Metrology for low-k materials", Silknet Aliance, 2003.

J.R. Levine Parrill, et al, "GISAXS—Glancing Incidence Small Angle X-ray Scattering", Journal de Physique IV 3 (Dec. 1993), pp. 411-417.

Jaklevic, et al., "High Rate X-Ray Fluorescence Analysis by Pulsed Excitation", IEEE Transactions on Nuclear Science NS-19:3 (1972), pp. 392-395.

Jaklevic, et al., "Small X-Ray Tubes for Energy Dispersive Analysis Using Semiconductor Spectrometers", Advances in X-Ray Analysis 15 (1972), pp. 266-275.

Jaklevic, et al., "Energy Dispersive X-Ray Fluorescence Spectrometry Using Pulsed X-Ray Excitation", Advances in X-Ray Analysis 19 (1976).

* cited by examiner

TARGET ALIGNMENT FOR X-RAY SCATTERING MEASUREMENTS

CROSS-REFERENCE TO RELATED APPLICATION

This application is a continuation-in-part of U.S. patent application Ser. No. 11/000,044, filed Dec. 1, 2004 now U.S. Pat. No. 7,474,732 (published as US 2006/0115046 A1), whose disclosure is incorporated herein by reference.

FIELD OF THE INVENTION

The present invention relates generally to non-destructive testing, and particularly to methods and systems for measuring properties of very small features on a substrate.

BACKGROUND OF THE INVENTION

When microelectronic devices are produced on a semiconductor wafer, it is crucial that the critical dimensions of the devices be held within specified tolerances. Critical dimensions, in this context, refer to the widths of features, such as conductors, that are deposited on the wafer and the spacing between adjacent features. Deviations from the specified dimensions lead to performance and yield degradation. Most microelectronic production facilities currently use optical metrology to monitor critical dimensions. As semiconductor devices become ever denser, however, with design rules of 0.25 μm and below, it is growing increasingly difficult for classical optical metrology systems to provide sufficiently accurate results.

X-ray measurement of critical dimensions has been proposed as an alternative to optical measurement. Systems and methods for this purpose are described, for example, in U.S. Pat. No. 6,556,652, whose disclosure is incorporated herein by reference. According to the method described in this patent, a surface of a substrate is irradiated with a beam of X-rays. A pattern of the X-rays scattered from the surface due to features formed on the surface is then detected and analyzed to measure a dimension of the features in a direction parallel to the surface.

Another method for X-ray based CD measurements is described by Jones et al., in "Small Angle X-ray Scattering for Sub-100 nm Pattern Characterization," *Applied Physics Letters* 83:19 (2003), pages 4059-4061, which is incorporated herein by reference. The authors use transmission-mode small angle X-ray scattering (SAXS) with a synchrotron X-ray source to characterize a series of polymer photoresist gratings formed on a substrate. The X-ray beam passes through the grating and the substrate, and the SAXS pattern is measured using a two-dimensional CCD detector. The photoresist grating produces a one-dimensional series of diffraction spots in the SAXS pattern on the detector. The SAXS intensity as a function of the scattering vector q is analyzed to determine the grating spacing and sidewall angle.

Alternatively, X-ray based CD measurements may be carried out in reflection mode, as described, for example, in U.S. Pat. No. 7,110,491, whose disclosure is incorporated herein by reference. A beam of X-rays is directed to impinge on the area of a periodic feature on a sample, and the X-rays scattered from the surface are detected as a function of azimuth. The scattered X-rays exhibit a pattern of diffraction, which is analyzed in order to extract information regarding the dimensions of the periodic feature.

SUMMARY OF THE INVENTION

In some X-ray scattering applications, such as diffraction measurements, a structure in the sample under test causes the X-rays to scatter in a pattern of parallel stripes. This sort of scattering pattern may advantageously be detected using an array of radiation detectors. To maximize detection resolution, it is desirable that the array be aligned so that the detectors in the array are oriented parallel to the stripes, or equivalently, that the sample be aligned so that the stripes are parallel to the detectors. The embodiments of the present invention that are described hereinbelow provide methods and systems for performing this sort of alignment. Although these embodiments relate specifically to X-ray diffraction and X-ray reflectometry, the principles of the present invention may likewise be applied in other types of X-ray scattering measurements, as well as in scattering of ionizing radiation in other energy ranges.

There is therefore provided, in accordance with an embodiment of the present invention, a method for X-ray analysis of a sample, including:

directing a beam of X-rays to impinge on a structure in the sample such that the X-rays are scattered from the structure in a pattern of stripes;

receiving the scattered X-rays using an array of detectors; and adjusting a relative alignment between the sample and the array so that the stripes are parallel to the detectors.

In some embodiments, the structure includes a periodic structure, and the pattern of stripes is a diffraction pattern due to scattering of the beam from the periodic structure. In one embodiment, the sample is a semiconductor wafer, and the structure includes a feature formed on a surface of the wafer, and receiving the scattered X-rays includes processing a signal that is output by the array of detectors so as to measure a critical dimension of the feature responsively to the diffraction pattern. In a disclosed embodiment, directing the beam includes transmitting the X-rays through a target area of the sample containing the structure, and receiving the scattered X-rays includes detecting the diffraction pattern in the X-rays that have been transmitted through the sample.

In a disclosed embodiment, adjusting the relative alignment includes setting an angle of rotation of the sample. Typically, setting the angle of rotation includes placing a test sample on an adjustable mount between a source of the X-rays and the array of detectors, the test sample including a region that is opaque to the X-rays and casts a shadow on the array, observing an output signal from the array of detectors while adjusting the mount so as to determine an alignment angle at which an edge of the shadow is parallel to the detectors, and placing the sample on the mount at the determined alignment angle in place of the test sample.

In another embodiment, the structure includes a thin film on a surface of the structure, and the pattern of stripes is an oscillatory pattern as a function of the elevation angle due to reflection of the X-rays from the surface.

In some embodiments, adjusting the relative alignment includes receiving an output signal from the array of detectors, detecting a transition in the output signal corresponding to an edge of a shadow that is cast on the array, and aligning at least one of the array and the sample responsively to the transition. Aligning the at least one of the detector array and the sample may include choosing an angle of alignment so as to maximize a sharpness of the transition.

In a disclosed embodiment, the array has an axis, and the detectors are elongated in a direction perpendicular to the axis, and adjusting the relative alignment includes aligning at least one of the sample and the array so that the stripes are parallel to the direction of elongation of the detectors.

There is also provided, in accordance with an embodiment of the present invention, apparatus for X-ray analysis of a sample, including:

an X-ray source, which is configured to direct a beam of X-rays to impinge on a structure in the sample such that the X-rays are scattered from the structure in a pattern of stripes;

an array of detectors, which is positioned to receive the scattered X-rays and to output a signal responsively thereto; and an alignment mechanism, which is configured to adjust a relative alignment between the sample and the array, responsively to the signal, so that the stripes are parallel to the detectors.

The present invention will be more fully understood from the following detailed description of the embodiments thereof, taken together with the drawings in which:

DETAILED DESCRIPTION OF EMBODIMENTS

Figure 1:
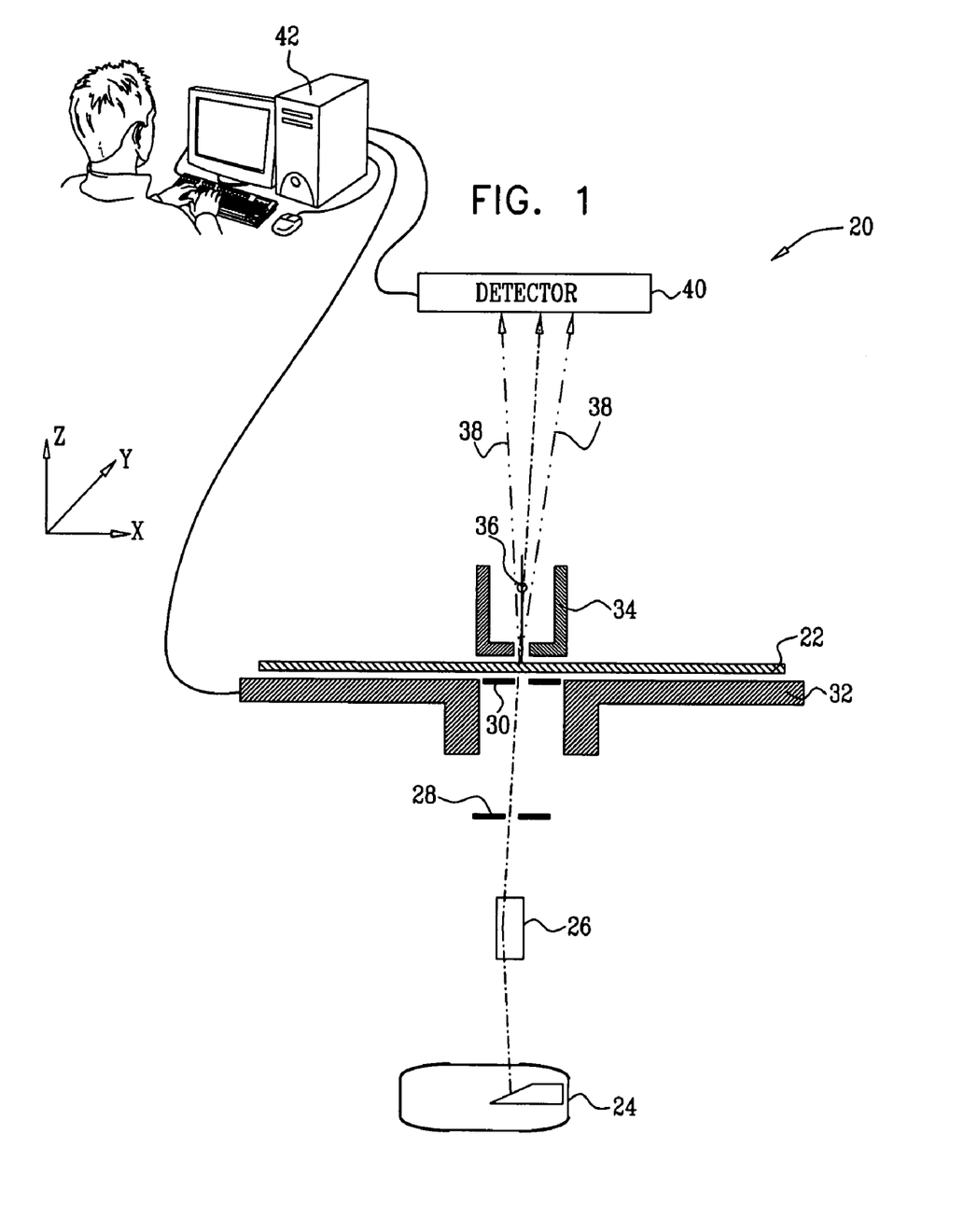
FIG. 1 is a schematic side view of apparatus for measurement of critical dimensions using X-rays, in accordance with an embodiment of the present invention.
Figure 2:
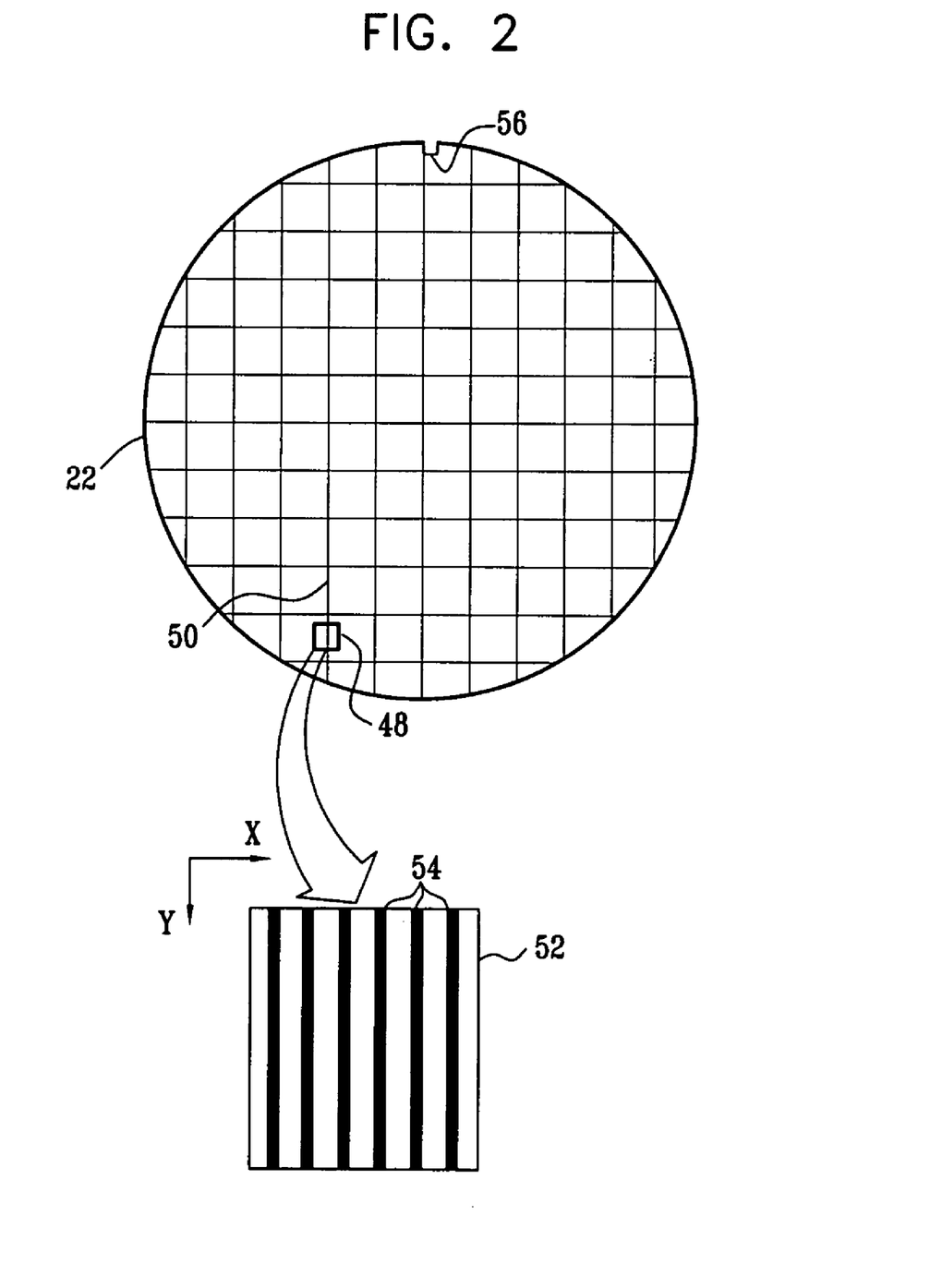
FIG. 2 is a schematic top view of a semiconductor wafer and a detail of a periodic pattern on the wafer, which is used in measuring critical dimensions in accordance with an embodiment of the present invention.

FIG. 1 is a schematic, pictorial illustration of a system 20 for measurement of critical dimensions on a semiconductor wafer 22, in accordance with an embodiment of the present invention. An X-ray source 24 emits a beam of X-rays, which is collimated by collimating optics 26 and directed onto a target area on wafer 22. A periodic test pattern is formed in the target area for purposes of critical dimension (CD) measurement. An exemplary test pattern that may be used for this purpose is shown in FIG. 2 and described hereinbelow with reference to that figure. For convenience in the description that follows, the Z-axis (as shown in FIG. 1) is defined by a line drawn between the X-ray source and the target area, and the test pattern is assumed to have a structure that varies periodically along the X-direction, in the plane of wafer 22.

Collimating optics 26 may comprise, for example, a doubly-curved mirror with a multilayer coating, which reflects the X-rays to create a beam with low divergence <0.3° and small spot size (typically <100 μm). Optics of this sort are available from various manufacturers, such as Applied X-ray Optics (AXO, Dresden, Germany). The beam collimation is further enhanced by passage through successive slits 28 and 30. Typically, these slits are oriented in the Y-direction (perpendicular to the plane of the page in FIG. 1), with a width of approximately 50 μm in the X-direction. The beam that is incident on wafer 22 may consequently be elongated in the Y-direction.

The test pattern in the target area on wafer 22 causes the X-rays that are transmitted through the wafer to be scattered into a diffraction pattern comprising multiple parallel stripes, which are oriented in the Y-direction and spaced apart along the X-direction. The spacing and amplitudes of the diffraction stripes are indicative of the critical dimensions of features on wafer 22, as expressed by the dimensions of the test pattern. Wafer 22 is typically mounted on a stage 32, which permits the orientation of the wafer, and hence of the stripes in the diffraction pattern, to be suitably adjusted and thus serves as an alignment mechanism, as described in detail hereinbelow. Additionally or alternatively, the alignment mechanism may be configured to adjust the positions and/or orientations of other elements of system 20.

Figure 3:
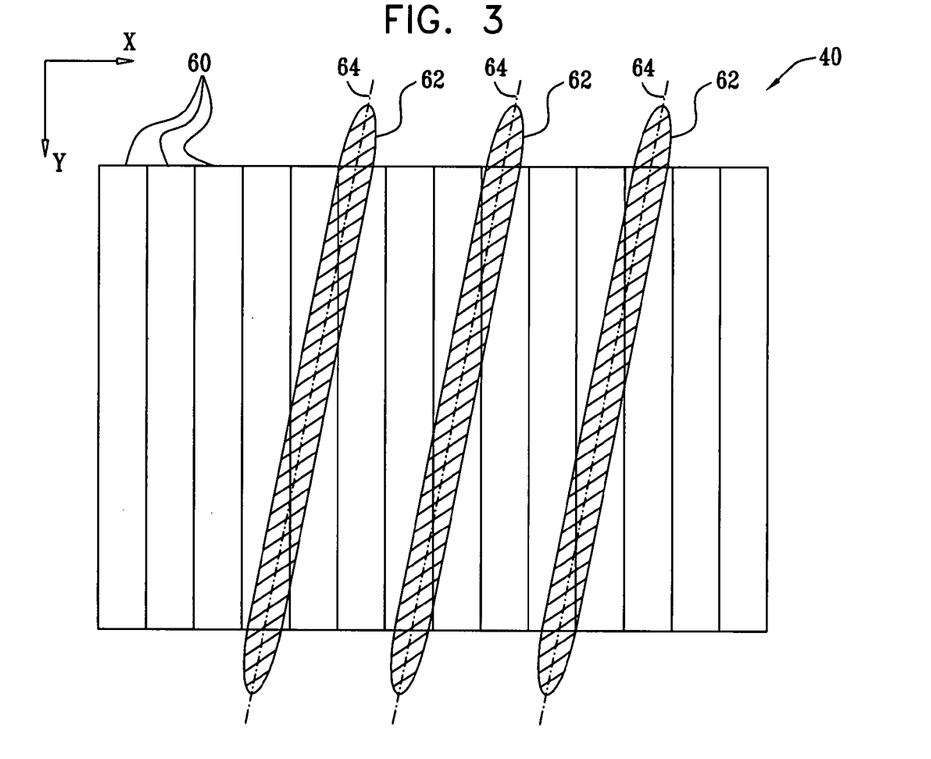
FIG. 3 is a schematic frontal view of a detector array showing an X-ray diffraction pattern projected onto the array, prior to alignment of the pattern with the array in accordance with an embodiment of the present invention.

X-rays 38 that are diffracted from wafer 22 pass through a pinhole 34, which blocks stray radiation, and are then incident on an X-ray detector array 40, such as a CCD array. The detector array is advantageous in being able to simultaneously receive and measure the scattered radiation over a range of angles. Details of the array and its detection of the scattered X-rays are described hereinbelow with reference to FIG. 3. A beam stop 36 is positioned along the axis of the irradiating X-ray beam in order to block the X-rays that pass directly through wafer 22 without diffraction. (These X-rays could otherwise overwhelm the much weaker diffraction signal at the detector array.) Pinhole 34 and beam stop 36 may also be elongated and aligned in the Y-direction, to match the elongated dimensions of the X-ray beam and diffraction pattern. Detector array 40 is typically similarly positioned so that the detectors in the array, as shown in FIG. 3, are aligned in this same Y-direction. An element of the motion assembly in system 20 (not shown in the figures) may be coupled to adjust the orientation of the detector array, as well as of the other components mentioned above.

Detector array 40 outputs a signal responsive to the flux of X-ray photons incident on each of the detectors in the array. The signal is received and analyzed by a signal processor 42, which preferably comprises a general-purpose computer equipped with suitable signal processing hardware and software. During an initial calibration phase, as described hereinbelow, the processor outputs a signal that is indicative of the relative alignment between wafer 22 and array 40. This signal is used in adjusting either the wafer (using stage 32) or the detector array, or both, for optimal alignment. The adjustment may be performed either fully automatically or with manual input by an operator of system 20.

After the alignment has been optimized, detector array 40 receives and measures X-rays scattered from the test pattern on wafer 22. The processor analyzes the diffraction spectrum of the scattered radiation and outputs a measurement of selected critical dimensions of the pattern on wafer 22. Methods for translating features of such diffraction patterns into CD measurements are known in the art, as described, for example, in the above-mentioned article by Jones, et al., and U.S. Pat. No. 7,110,491, and are beyond the scope of the present patent application. Although system 20 is shown in FIG. 1 in a stand-alone configuration, the system may alternatively be integrated into a cluster tool or semiconductor processing chamber, as described, for example, in U.S. Pat. No. 7,110,491, for purposes of in situ process measurements.

FIG. 2 schematically shows details of wafer 22, and specifically of a periodic pattern 52 formed in a target area 48 of the wafer, in accordance with an embodiment of the present invention. Pattern 52 in this example comprises a grating of parallel linear elements, such as ridges 54. In the alignment procedure that is described hereinbelow, these linear elements are aligned precisely along the Y-direction, as shown in the figure. Pattern 52 may be a special test pattern, which is formed on a scribe line 50 between adjacent dies on wafer 22 for use in CD measurement. In this case, ridges 54 are typically formed by the same processes of material deposition, photolithography and etching as are functional circuit features on the wafer that pattern 52 is intended to test. Details of the formation and use of this sort of pattern in CD measurements are given in the above-mentioned article by Jones, et al., and U.S. Pat. No. 7,110,491. Alternatively, pattern 52 may comprises an actual, functional pattern within the dies on the wafer.

Wafer 22 comprises an alignment notch 56. The notch is created on all wafers of a given type in a position that is precisely fixed relative to the dies on the wafer and to scribe lines 50 between the dies. Therefore, once the proper angular alignment of pattern 52 has been determined for one wafer, subsequent wafers can be aligned simply on the basis of the notch location, without requiring that the full alignment procedure be repeated for all wafers.

FIG. 3 is a schematic frontal view of detector array 40, showing an X-ray diffraction pattern as it might be projected onto the array prior to alignment of wafer 22 in accordance with an embodiment of the present invention. Array 40 in this embodiment comprises a row of parallel detectors 60. The diffraction pattern comprises stripes 62, having parallel stripe axes 64, whose orientation is parallel to the orientation of ridges 54 in pattern 52 (FIG. 2). Although the stripes in FIG. 3 are shown as distinct, sharply-defined areas, in practice the "stripes" in a diffraction pattern are simply parallel elongated areas of relatively high intensity of scattered radiation, separated by areas of relatively lower intensity. The term "stripes," in the context of the present patent application and in the claims, should therefore be understood in this broader sense. Stripes of this sort may be observed in other types of X-ray scattering, such as the periodic stripes that appear as a function of elevation angle in the oscillatory pattern of low-angle X-ray reflections from a surface on which a thin film has been formed. Reflection patterns of this sort and their measurement are described, for example, in the above-mentioned U.S. patent application Ser. No. 11/000,044.

Detectors 60 in array 40 are elongated in the Y-direction and relatively closely spaced in a single row along the array axis in the X-direction. For example, in one embodiment, array 40 may comprise a row of detectors each 24 µm wide in the X-direction and 6 mm high in the Y-direction. Alternatively, the array may comprise a two-dimensional matrix of detector elements. In this latter case, the elements in each column (along the Y-direction) may be binned together to form "virtual detectors" having the elongated shape that is shown in FIG. 3. This elongated shape is advantageous in capturing a larger portion of each stripe 62 in the corresponding detector, thus enhancing the signal strength and improving the signal/noise ratio and throughput of system 20.

The difficulty in using elongated detectors of this sort, however, is that misalignment between detectors 60 and axes 64 of stripes 62 reduces the resolution of detection of the diffraction pattern. In the misaligned configuration shown in FIG. 3, the signal due to each stripe is spread over multiple detectors 60. If axes 64 were properly aligned with the detectors, each stripe would fall across a smaller number of the detectors, and the resulting diffraction pattern measured by processor 42 would be sharper and would therefore provide a more accurate indication of the critical dimensions in pattern 52.

Figure 4:
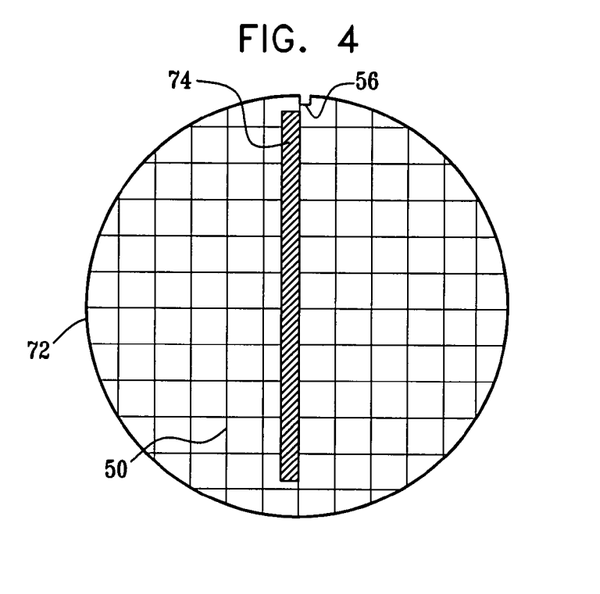
FIG. 4 is a schematic top view of a target used in aligning a semiconductor wafer with a detector array, in accordance with an embodiment of the present invention.
Figure 5:
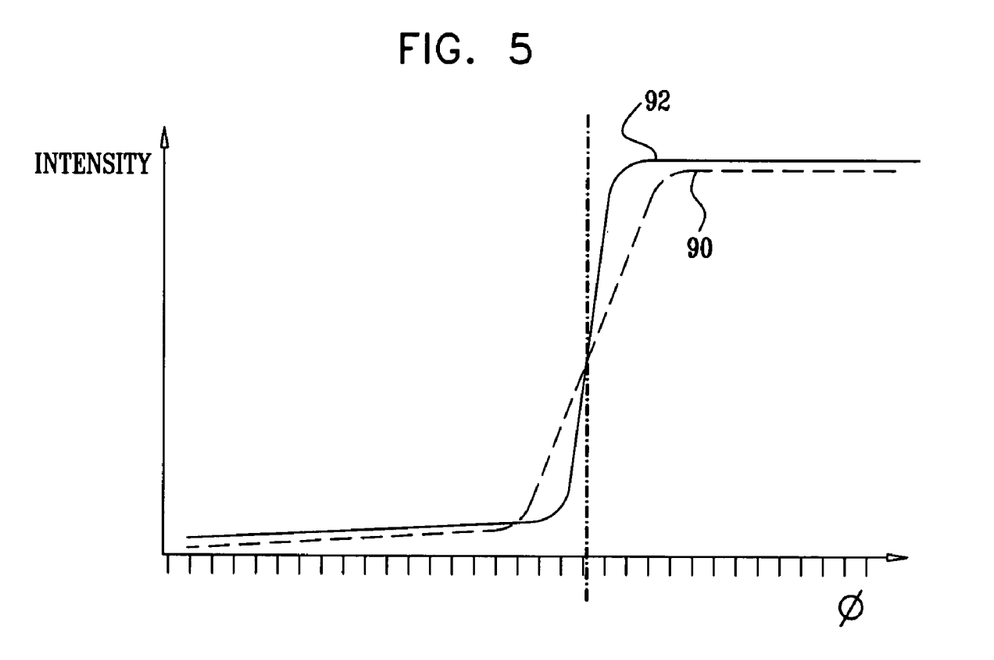
FIG. 5 is a schematic plot of X-ray intensity measured by a detector array in two different orientations of the target of FIG. 4, in accordance with an embodiment of the present invention.

Reference is now made to FIGS. 4 and 5, which schematically illustrate a procedure for aligning wafer 22 relative to detector array 40, in accordance with an embodiment of the present invention. The object of this procedure is to align axes 64 of stripes 62 with detectors 60. FIG. 4 is a schematic top view of a test wafer 72, which serves as a test sample in place of wafer 22 in the alignment procedure, while FIG. 5 is a schematic plot of the X-ray intensity measured by array 40 in two different orientations of test wafer 72.

Test wafer 72 is identical in shape and size to wafer 22, with notch 56 in the same position. An X-ray opaque region, such as a metal ruler 74, is fixed precisely to test wafer 72, with the edge of the ruler parallel to the direction of ridges 54 of pattern 52 on wafer 22. The requisite parallelism may be achieved, for example, by manually gluing the ruler to the wafer along one of scribe lines 50. This simple procedure is capable of aligning the ruler with the axis of pattern 52 to within about 2 mrad. This level of accuracy is adequate for CD measurements in system 20, since for this purpose it is sufficient that axes 64 be parallel to detectors 60 to within about 4 mrad. Alternatively, the metal plate may be more accurately placed, machined, or deposited on test wafer 72 in an automated or semi-automated procedure if necessary.

Test wafer 72 is placed on stage 32, and the stage is then rotated to align ruler 74 parallel to detectors 60. Alternatively or additionally, detector array 40 may be rotated for this purpose (although this option is less practical if the incident X-ray beam is already elongated, as described above, and array 40 is pre-aligned with the long axis of the beam). To align the ruler with the detectors, the test wafer is irradiated with a collimated beam of X-rays from source 24, and the shadow cast by the ruler is observed using the signal output by the detector array to processor 42. During this procedure, wafer 72 is typically shifted in the Z-direction from the normal measurement position at the focus of the X-ray beam toward array 40. (If wafer 72 is located at the beam focus, the edge of the shadow that is cast by ruler 74 is not sufficiently sharp.) The wafer may be shifted by appropriate operation of stage 32. In one typical measurement configuration, for example, the distance between wafer 22 and array 40 is about 85 cm, and wafer 72 is shifted 20 cm closer to the array during the alignment procedure.

The result of this sort of observation is shown in FIG. 5, which plots the X-ray intensity as a function of angle φ (i.e., as a function of detector position along the X-axis). The X-ray flux measured by detectors 60 that are in the shadow of the ruler (on the left side in the figure) is low, while the detectors that are not shielded by the ruler receive a high flux. A trace 90 in FIG. 5 corresponds to the signal output by array 40 before test wafer 72 has been properly aligned, while a trace 92 corresponds to the signal when the test wafer is properly aligned, with ruler 74 parallel to detectors 60. Trace 92 is characterized by a sharp transition from low to high intensity at the edge of the ruler. In trace 90, however, the transition is more gradual, since detectors 60 near the edge of the shadow are partly exposed to the incident X-rays and partly obscured by ruler 74.

In order to align test wafer 72, stage 32 is operated to rotate the test wafer until the edge of the shadow is aligned parallel to detectors 60. For this purpose, processor 42 may monitor the sharpness of the transition from low to high flux in the intensity trace of FIG. 5. The angular orientation of test wafer 72 is then fixed at the angle that gives the sharpest transition, meaning that the edge of the shadow is parallel to detectors 60. Alternatively, if array 40 comprises a two-dimensional matrix of detector elements (which are binned during the actual diffraction measurement, as described above), a two-dimensional image or readout of the intensity of X-rays incident on the array may be monitored. In this case, the angular orientation is fixed at the angle at which the edge marking the transition between high and low intensity regions in the image is aligned with a column of the detector elements. In either case, the location of notch 56 in this orientation is recorded. In subsequent CD measurements on wafers 22, stage 32 is rotated so that the notch is in this same location, thus ensuring proper alignment of pattern 52 with detector array 40.

Although the embodiments described above relate to measurements made on semiconductor wafer 22, the principles of the system and method described above may similarly be applied to samples of other types.

Similar principles of alignment may also be used in other X-ray scattering applications. For example, for optimal angular resolution in X-ray reflectometry (XRR) measurements, it is desirable that the orientation of the detector array be adjusted relative to the surface of the sample so that the axis of the array (the X-axis in FIG. 3) is precisely perpendicular to the sample surface. To perform the necessary alignment, the sample is irradiated with an incident beam at a grazing angle, i.e., roughly parallel to the surface of the sample. As a result, the X-ray flux measured by detectors that are above the plane of the surface is high, while that measured by the elements below the plane is low. The measurement as a function of angle has the general form shown in FIG. 5. The desired alignment can be achieved by adjusting the orientation angle of the detector array and/or the tilt angle of the sample so as to sharpen the transition in the intensity profile. Further details of this technique are presented in the above-mentioned U.S. patent application Ser. No. 11/000,044.

As another example, the principles of alignment that are described above may be used in X-ray fluorescence (XRF) analysis, including particularly grazing emission XRF, as well as other XRF techniques known in the art. Grazing emission XRF is described, for example, in an article by Wiener et al., entitled "Characterization of Titanium Nitride Layers by Grazing-Emission X-ray Fluorescence Spectrometry," in *Applied Surface Science* 125 (1998), p. 129, which is incorporated herein by reference. Additionally or alternatively, these techniques may be used in small-angle scattering measurements, as described in U.S. Pat. No. 6,895,075, whose disclosure is incorporated herein by reference, as well as in reflection-mode diffraction measurements, as described in the above-mentioned U.S. Pat. No. 7,110,491. Furthermore, the principles of system 20 may be implemented in position-sensitive detection systems for other energy ranges, such as for detection of gamma rays and other nuclear radiation.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for X-ray analysis of a sample, comprising:
   directing a beam of X-rays to impinge on a structure in the sample such that the X-rays are scattered from the structure in a pattern of stripes;
   receiving the scattered X-rays using an array of detectors; and
   adjusting a relative alignment between the sample and the array so that the stripes are parallel to the detectors.

2. The method according to claim 1, wherein the structure comprises a periodic structure, and wherein the pattern of stripes is a diffraction pattern due to scattering of the beam from the periodic structure.

3. The method according to claim 2, wherein the sample is a semiconductor wafer, and wherein the structure comprises a feature formed on a surface of the wafer, and wherein receiving the scattered X-rays comprises processing a signal that is output by the array of detectors so as to measure a critical dimension of the feature responsively to the diffraction pattern.

4. The method according to claim 2, wherein directing the beam comprises transmitting the X-rays through a target area of the sample containing the structure, and wherein receiving the scattered X-rays comprises detecting the diffraction pattern in the X-rays that have been transmitted through the sample.

5. The method according to claim 4, wherein adjusting the relative alignment comprises setting an angle of rotation of the sample.

6. The method according to claim 5, wherein setting the angle of rotation comprises:
   placing a test sample on an adjustable mount between a source of the X-rays and the array of detectors, the test sample comprising a region that is opaque to the X-rays and casts a shadow on the array;
   observing an output signal from the array of detectors while adjusting the mount so as to determine an alignment angle at which an edge of the shadow is parallel to the detectors; and
   placing the sample on the mount at the determined alignment angle in place of the test sample.

7. The method according to claim 1, wherein the structure comprises a thin film on a surface of the structure, and wherein the pattern of stripes is an oscillatory pattern as a function of the elevation angle due to reflection of the X-rays from the surface.

8. The method according to claim 1, wherein adjusting the relative alignment comprises:
   receiving an output signal from the array of detectors;
   detecting a transition in the output signal corresponding to an edge of a shadow that is cast on the array; and
   aligning at least one of the array and the sample responsively to the transition.

9. The method according to claim 8, wherein aligning the at least one of the detector array and the sample comprises choosing an angle of alignment so as to maximize a sharpness of the transition.

10. The method according to claim 1, wherein the array has an axis, and wherein the detectors are elongated in a direction perpendicular to the axis, and wherein adjusting the relative alignment comprises aligning at least one of the sample and the array so that the stripes are parallel to the direction of elongation of the detectors.

11. Apparatus for X-ray analysis of a sample, comprising:
    an X-ray source, which is configured to direct a beam of X-rays to impinge on a structure in the sample such that the X-rays are scattered from the structure in a pattern of stripes;
    an array of detectors, which is positioned to receive the scattered X-rays and to output a signal responsively thereto; and an alignment mechanism, which is configured to adjust a relative alignment between the sample and the array, responsively to the signal, so that the stripes are parallel to the detectors.

12. The apparatus according to claim 11, wherein the structure comprises a periodic structure, and wherein the pattern of stripes is a diffraction pattern due to scattering of the beam from the periodic structure.

13. The apparatus according to claim 12, wherein the sample is a semiconductor wafer, and wherein the structure comprises a feature formed on a surface of the wafer, and wherein the apparatus comprises a signal processor, which is coupled to process the signal so as to measure a critical dimension of the feature responsively to the diffraction pattern.

14. The apparatus according to claim 12, wherein the X-ray source is configured to direct the beam through a target area of the sample containing the structure, and wherein the array of detectors is configured to detect the diffraction pattern in the X-rays that have been transmitted through the sample.

15. The apparatus according to claim 14, wherein the alignment mechanism comprises an adjustable mount, which is configured to set an angle of rotation of the sample.

16. The apparatus according to claim 15, and comprising a test sample, which comprises a region that is opaque to the X-rays, and wherein the alignment mechanism is operated by placing the test sample on the adjustable mount so that the opaque region casts a shadow on the array, and observing the signal output by the array of detectors while adjusting the mount so as to determine an alignment angle at which an edge of the shadow is parallel to the detectors, and subsequently placing the sample on the mount at the determined alignment angle in place of the test sample.

17. The apparatus according to claim 11, wherein the structure comprises a thin film on a surface of the structure, and wherein the pattern of stripes is an oscillatory pattern as a function of the elevation angle due to reflection of the X-rays from the surface.

18. The apparatus according to claim 11, wherein the alignment mechanism is operated by detecting a transition in the signal corresponding to an edge of a shadow that is cast on the array, and aligning at least one of the array and the sample responsively to the transition.

19. The apparatus according to claim 18, wherein an angle of alignment between the array and the sample is chosen so as to maximize a sharpness of the transition.

20. The apparatus according to claim 11, wherein the array has an axis, and wherein the detectors are elongated in a direction perpendicular to the axis, and wherein the alignment mechanism is configured to align at least one of the sample and the array so that the stripes are parallel to the direction of elongation of the detectors.

* * * * *